Figure 1:
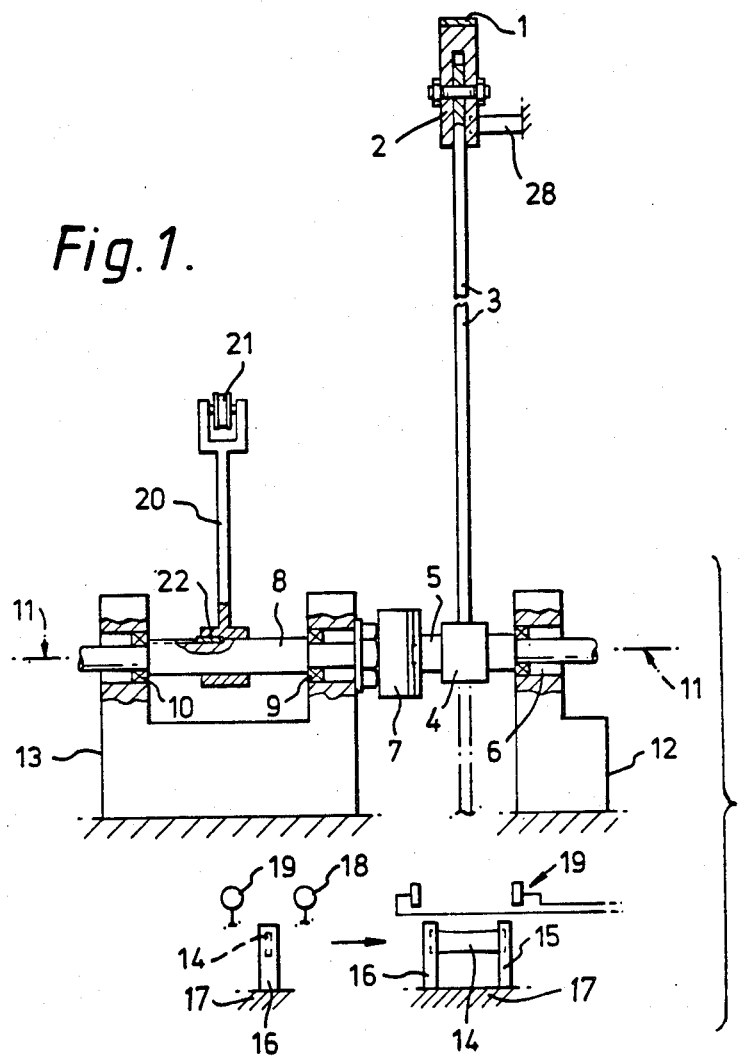

United States Patent [19]
Isherwood et al.

[11] Patent Number: 4,546,654
[45] Date of Patent: Oct. 15, 1985

[54] IMPACT TESTING MACHINE

[75] Inventors: David P. Isherwood, Bradfield; Hany R. Younan, London, both of England

[73] Assignee: National Research Development Corporation, London, England

[21] Appl. No.: 528,474

[22] Filed: Sep. 1, 1983

[30] Foreign Application Priority Data
Sep. 2, 1982 [GB] United Kingdom ............. 8224980

[51] Int. Cl.⁴ ............................................. G01N 3/30
[52] U.S. Cl. .......................................... 73/844; 73/12
[58] Field of Search ................... 73/12, 82, 87, 844

[56] References Cited
U.S. PATENT DOCUMENTS
2,022,666 12/1935 Haskell et al. ................ 73/844
2,188,898 2/1940 Haskell et al. ................ 73/844
2,398,746 4/1946 Kanter et al. ............... 73/844 X

FOREIGN PATENT DOCUMENTS
0462100 8/1975 U.S.S.R. ....................... 73/12

Primary Examiner—Charles A. Ruehl
Attorney, Agent, or Firm—Cushman, Darby & Cushman

[57] ABSTRACT

An impact testing machine in which a striker held by a fixed mounting is struck by a striker carried by a pivoted arm. A motor, connected to the arm by a clutch, accelerates the arm at such a rate that the striker achieves useful speed within one revolution from stationary, and the clutch operates to disengage motor and arm just before the striker hits the specimen so that the momentum of strike is independent of the motor. Various constructions and arrangements of motor and arm are disclosed whereby the necessary high angular acceleration may be imparted to the arm, including a lost-motion connection using a reeled wire bearing upon a pulley.

2 Claims, 2 Drawing Figures

IMPACT TESTING MACHINE

This invention relates to impact testing machines, in which material specimens are fractured by the impact of a striker. Measurements are made to determine the values of the kinetic energy of the striker immediately before and after impact, so that the energy required to effect the fracture can be related to the difference between those two values. From the energy required to effect the fracture, much useful information relating to the strength and structure of the specimen may be obtained.

In most known impact testers the striker is either shot at the specimen from a gun, or carried on the end of a pendulum. The gun-type instruments have the advantage that high kinetic energy can easily be imparted to the striker before it hits the specimen: the striker may therefore retain considerable energy even after impact, and the magnitude of the energy levels before and after will be such that the difference between them can be measured easily and with accuracy. A disadvantage of such instruments, however, is that for reasons of safety and accuracy of aim the striker has to be propelled down guiding tubes: glancing impact with the walls of these tubes diminishes the energy of the striker and leads to inconsistency between one test and the next because the pattern of impact between the striker and the tube walls will inevitably vary between tests.

In the other known type of machine in which the striker is carried on the end of a pendulum arm and makes impact with the specimen as the arm reaches the bottom of its swing, consistency of energy levels in successive tests is easier to achieve because the motion of the pendulum is less subject to variation. To give the striker energy levels comparable with those that can be given by a gun, however, the pendulum arm must be long and heavy and must be dropped from a considerable height. Such machines therefore tend to be large.

The present invention seeks to provide a relatively compact machine by which the striker can be accelerated to variable but high velocity, of accurate and predetermined value. According to the invention an impact tester comprises a striker held by a pivoted arm, a motor adapted to be connected to that arm and to give it angular acceleration at such rate that the striker reaches a useful speed for impact testing within one revolution of the arm, a mounting to hold a specimen in the path of the striker, and clutch or like means to disconnect the motor from the arm before the striker hits the specimen.

The motor may be an electric motor of variable running speed and high acceleration. Alternatively the motor may be connected to the arm by way of gearing or some other mechanism which affords mechanical advantage, so that the angular acceleration of the motor is reflected in enhanced acceleration of the striker. Disengaging a clutch may also allow the motor to run up to speed before being connected to the arm.

The connection between the motor and the arm may also include a lost-motion device so that drive is not transmitted to the arm simultaneously with the engagement of the clutch, but only subsequently after the lost motion has been taken up.

The shaft carrying the striker arm may also carry an arm of shorter length, having at its end a pulley which co-operates with a wire anchored at one end and fastened at the other to a reel driven by the motor through a clutch. When the clutch is first engaged the wire may be slack, so that the wire only begins to exert leverage upon the shorter arm when it becomes taught, and engagement of the clutch is already complete. The clutch may later be disengaged to disconnect motor and reel before the position is reached in which the wire can give no more and so is at risk of either stopping the motor dead or breaking under the force exerted by the motor. Means (which may include yet a further clutch) may be provided to disconnect the drive between motor and striker arm before the striker makes impact with the specimen, so that the arm and associated parts are rotating freely and under their own undriven momentum when impact takes place. Photocells or other speed sensors may be mounted to either side of the specimen so that the energy lost by the striker due to impact may be determined from the difference in velocity of the striker before and after impact.

Figure 2:
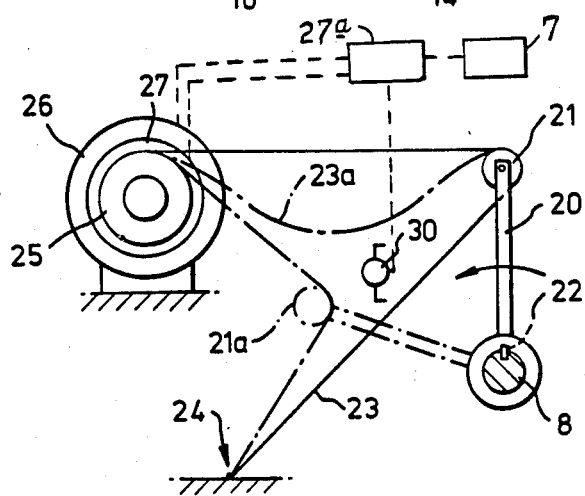

The invention is also defined by the claims the disclosure of which should be read as part of the disclosure of this specification. The invention will now be described, by way of example, with reference to the accompanying diagrammatic drawings in which:

FIG. 1 is an elevation of part of an apparatus including the striker arm and shaft and the mounted specimen, with some added fragmentary views, and FIG. 2 is a view, taken in a direction parallel to the shaft, of the motor, wire and associated parts.

A striker 1 is held in a holder 2 mounted at one end of a long arm 3. By a coupling member 4 at its other end the arm 3 is connected to a shaft 5 mounted at one end in a bearing 6 and connected at the other to one half of a magnetic clutch 7. The other half of clutch 7 is connected to a shaft 8 mounted in bearings 9 and 10. Reference 11 indicates the common axis of shafts 5 and 8.

A clearance between the supporting structure 12 of bearing 6 and the supporting structure 13 of bearings 9 and 10 allows arm 3 to rotate through a full revolution. Arm 3 is shown in the vertically upward position in FIG. 1, and a specimen 14 is mounted in supports 15, 16 mounted on fixed structure 17 and located diametrically opposite to where striker 1 is shown in the Figure, so that the specimen 14 will be shattered by the striker 1 when the latter passes through the lowest point of its revolution. Photocell pairs 18 and 19, located respectively just before and after the specimen 14 in relation to the rotation of arm 3, are connected to conventional timing equipment (not shown) to record the angular velocity of striker 1 just before and after making impact with the specimen. From the difference between the speeds a measure may be obtained of the energy lost by the striker, arm and associated parts due to the impact, and hence of quantities related to the strength and structure of the specimen 14. By being held at both ends by supports 15, 16 as shown, the specimen is set up in the manner customary for the known Charpy impact test, but it would equally be possible for the specimen to be set up with one end embedded in structure 17 so that the other end projected free from that structure in cantilever fashion and lay within the path of striker 1. With the specimen supported thus, the characteristics of the impact test would be more similar to those of the known Izod type.

Between bearings 9 and 10 a shorter arm 20, carrying a pulley 21, is keyed to shaft 8 at 22. As FIG. 2 shows best a wire 23, anchored to fixed structure at 24, passes around pulley 21 and onto a reel 25 driven by a motor 26 by way of a magnetic clutch 27 interposed coaxially between reel and motor.

A test begins with arm 3 substantially vertical—perhaps just over-centre, and supported against a deflectable stop 28—with clutches 7 and 27 disengaged and with wire 23 slack between pulley 21 and reel 25 as shown in broken line at 23a in FIG. 2. Motor 26 is then run up to a predetermined speed. When that speed is reached, clutches 7 and 27 are simultaneously engaged by speed responsive operating means indicated at 27a. The slack 23a in wire 23 is quickly taken up, after which the shortening wire bears against pulley 21, causing arm 20 and shaft 8 to rotate about axis 11 with rapid angular acceleration. Because shafts 5 and 8 are connected by engaged clutch 7, and because of the mechanical advantage resulting from arm 3 being much longer than arm 20, the linear acceleration of holder 2 and striker 1 is even greater than that of pulley 21. Before pulley 21 reaches the position indicated at 21a, at which the length of wire 23 between anchorage 24 and reel 25 would be a minimum and the wire would therefore either abruptly brake the motor 26 or snap, a pair of photocells 30 whose beam is interrupted by the passage of arm 20 operates by operating means 27a to disengage clutches 7, 27 again. Shafts 5 and 8 are therefore disconnected, and rotation of shaft 8 and arm 20 is quickly but gently arrested by contact between pulley 21 and wire 23 which the spinning reel 25, although now undriven, still tends to wind in. Arm 3, together with shaft 5 and one half of clutch 7, continues to rotate undriven under its own acquired momentum, and when it reaches the lowest point of its revolution the striker 1 makes impact with specimen 14 as already described. Once the specimen is broken the arm 3 may continue to rotate until it comes to rest, with the holder brushing past stop 28 once per revolution.

In an alternative construction clutch 7 could be omitted so that shafts 5 and 8 became a single continuous shaft, and coupling 4 could be a simple, over-run clutch type of connection between arm 3 and shaft 5 so that as the latter was arrested when pulley 21 reached the position 21a, the arm 3 would continue to rotate under its own momentum. The invention also includes the alternative type of apparatus in which motor 26, which is of conventional performance, is replaced by a more sophisticated motor which is capable of rapid acceleration to a variable but accurately ascertainable speed, and which could be connected to shaft 5 by way of a single clutch which disengages shortly before the striker makes impact with the specimen.

We claim:

1. An impact testing machine comprising:

a pivoted arm;

a striker held by said pivoted arm;

mounting means adapted to hold a specimen in the path of said striker arm when said striker is moved by the pivoting of said pivoted arm;

motor means connected to said pivoted arm and to give said arm angular acceleration sufficient for said striker to reach a useful speed for impact testing within one revolution of said pivoted arm from stationary, and clutch means to disengage said motor means from said pivoted arm after accelerating it and just before said striker meets a specimen when held by said mounting means, said machine further including operating means for said clutch means adapted to engage said clutch means so that said pivoted arm is connected to said motor means only after said motor means has run up to speed, said machine further including a lost-motion device connecting said motor means to said pivoted arm, whereby drive is not transmitted from said motor means to said pivoted arm simultaneously with the engagement of said clutch but only subsequently after said lost motion has been taken up.

2. An impact testing machine according to claim 1 including a pulley and a wire, and a reel driven by said motor means, and in which said lost-motion device includes a lever arm associated with said pivoted arm but of shorter length, said pulley being carried by said lever arm and co-operating with said wire, and in which said wire is anchored at one end and is fastened at the other to said reel.

* * * * *